United States Patent
Nashner (10) Patent No.: US 7,179,234 B2
(45) Date of Patent: Feb. 20, 2007

(54) APPARATUS AND METHOD FOR CHARACTERIZING CONTRIBUTIONS OF FORCES ASSOCIATED WITH A BODY PART OF A SUBJECT

(75) Inventor: Lewis M. Nashner, Portland, OR (US)

(73) Assignee: NeuroCom International, Inc., Clackamas, OR (US)

( * ) Notice: Subject to any disclaimer, the term of this patent is extended or adjusted under 35 U.S.C. 154(b) by 101 days.

(21) Appl. No.: 10/889,303

(22) Filed: Jul. 12, 2004

(65) Prior Publication Data

US 2005/0043661 A1   Feb. 24, 2005

Related U.S. Application Data

(60) Provisional application No. 60/486,055, filed on Jul. 10, 2003.

(51) Int. Cl.
*A61B 5/103* (2006.01)
*A61B 5/117* (2006.01)

(52) U.S. Cl. .......................... 600/595; 600/587
(58) Field of Classification Search ............... 600/587, 600/595
See application file for complete search history.

(56) References Cited

U.S. PATENT DOCUMENTS

| | | | | |
|---|---|---|---|---|
| 3,976,057 A | * | 8/1976 | Barclay | 601/34 |
| 4,586,495 A | * | 5/1986 | Petrofsky | 602/2 |
| 4,697,808 A | * | 10/1987 | Larson et al. | 482/51 |
| 4,830,024 A | | 5/1989 | Nashner et al. | 128/787 |
| 4,838,272 A | * | 6/1989 | Lieber | 607/48 |
| 5,052,406 A | | 10/1991 | Nashner | 128/782 |
| 5,112,296 A | * | 5/1992 | Beard et al. | 602/28 |
| 5,244,441 A | | 9/1993 | Dempster et al. | 482/9 |
| 5,269,318 A | | 12/1993 | Nashner | 128/782 |
| 5,303,715 A | | 4/1994 | Nashner et al. | 128/782 |
| 5,429,140 A | * | 7/1995 | Burdea et al. | 600/587 |
| 5,474,087 A | | 12/1995 | Nashner | 128/782 |
| 5,476,103 A | | 12/1995 | Nashner | 128/782 |
| 5,476,441 A | * | 12/1995 | Durfee et al. | 602/23 |
| 5,551,445 A | | 9/1996 | Nashner | 128/782 |
| 5,623,944 A | | 4/1997 | Nashner | 128/779 |
| 5,697,791 A | | 12/1997 | Nashner et al. | 434/247 |
| 5,980,429 A | | 11/1999 | Nashner | 482/8 |
| 5,980,435 A | * | 11/1999 | Joutras et al. | 482/114 |
| 6,010,465 A | | 1/2000 | Nashner | 600/595 |
| 6,190,287 B1 | | 2/2001 | Nashner | 482/8 |
| 6,592,538 B1 | * | 7/2003 | Hotchkiss et al. | 602/26 |
| 6,599,255 B2 | | 7/2003 | Zhang | 600/587 |

(Continued)

OTHER PUBLICATIONS

International Search Report mailed on Jan. 18, 22005 and prepared for International Application No. PCT/US0422180 International Filing Date of Jul. 12, 2004.

(Continued)

*Primary Examiner*—Max F. Hindenburg
*Assistant Examiner*—Rene Towa
(74) *Attorney, Agent, or Firm*—Bromberg & Sunstein LLP (57) ABSTRACT

A method and apparatus for characterizing contributions of forces associated with a body part of a subject when the body part is involved in movement is provided. The method includes causing movement of the body part in a prescribed manner and monitoring quantities related to at least one of displacement of the body part and external force on the body part. At least one quantity related to a force contribution associated with the body part is determined from the quantities measured.

13 Claims, 4 Drawing Sheets

U.S. PATENT DOCUMENTS

| | | |
|---|---|---|
| 6,632,158 B1 | 10/2003 | Nashner .................. 482/8 |
| 6,706,003 B2 | 3/2004 | Perrad et al. .............. 600/587 |
| 6,743,187 B2 | 6/2004 | Solomon et al. ........... 600/587 |
| 6,872,187 B1 * | 3/2005 | Stark et al. ................ 602/16 |
| 2004/0127337 A1 | 7/2004 | Nashner .................. 482/100 |
| 2005/0043661 A1 | 2/2005 | Nashner .................. 602/26 |

OTHER PUBLICATIONS

Edward Taub et al., Constraint-Induced Movement Therapy: A New Family of Techniques with Broad Application to Physical Rehabilitation—A Clinical Review *Journal of Rehabilitation Research and Development*, Jul. 1999, vol. 36, No. 3; pp. 237-251.

Serge Rossignol et al., New approaches to locomotor rehabilitation in spinal cord injury. *Annals of Neurology*, May 1995 vol. 37, No. 5; pp. 555-556.

Bruce H. Dobkin, An overview of treadmill locomotor training with partial body weight support: a neurophysiologically sound approach whose time has come for randomized clinical trials. *Neurorehabilitation and Neuronal Repair*, 1999; vol. 13, No. 3; 157-165.

Eric R. Kandel et al., *Principles of Neural Science*. editors. Elsevier/North Holland, New York, pp. 293-304.

* cited by examiner

APPARATUS AND METHOD FOR CHARACTERIZING CONTRIBUTIONS OF FORCES ASSOCIATED WITH A BODY PART OF A SUBJECT

The present application claims priority from U.S. Provisional Application No. 60/486,055, filed Jul. 10, 2003, which is hereby incorporated herein, in its entirety, by reference.

TECHNICAL FIELD

The present invention relates to stimulation of neural tissue and, in particular, to methods and apparatuses for causing prescribed movement of a portion of a subject's body using a mechanical device.

BACKGROUND ART

In individuals with substantial damage to the central nervous system ("CNS"), the traditional understanding has been that the damaged CNS tissue cannot readily regenerate. As a consequence, it has been further understood that the possibility of substantial recovery of daily life functional capabilities is highly unlikely in individuals with severe paralysis of the legs and/or arms caused by CNS diseases such as strokes, spinal cord injuries, and traumatic brain injuries.

New hope for individuals with CNS damage has been provided by recent research studies demonstrating regeneration of substantially damaged CNS pathways controlling the sensory and motor activities of the limbs (Taub Edward, PhD; Gitendra Uswatte, MA; Rama Pidikiti, MD. Constraint-Induced Movement Therapy: A New Family of Techniques with Broad Application to Physical Rehabilitation—A Clinical Review. *Journal of Rehabilitation Research and Development* 1999; 37). Frequent stimulation of damaged neural pathways has been cited as a critical factor to CNS tissue regeneration. For individuals with paralysis concentrated in the limbs on one side of the body, one approach to providing the necessary stimulation therapy is to force the subject to use the impaired limbs by constraining use of the unimpaired ones while the patient performs simple tasks. For individuals with incomplete bilateral paralysis, including paraplegic and quadriplegic injuries, spastic paralysis, multiple sclerosis, stroke, and traumatic brain injuries, locomotion therapy using a treadmill and a partial weight bearing harness has become an accepted standard of care (Rossignol IS, Barbeau H. New approaches to locomotor rehabilitation in spinal cord injury. Annals of Neurology 1995;37(5):555–556). In this type of therapy, the overhead harness system supports the patient sufficiently such that the motion of the treadmill belt assists the patient in moving the legs in a locomotor-like pattern. Such partial weight bearing treadmill methods are of proven clinical value in restoring the ability to move and walk in patients with unilateral paralysis and/or with sufficient residual function to generate a minimum level of limb movement in response to the treadmill belt motion (Dobkin BH. An overview of treadmill locomotor training with partial body weight support: a neurophysiologically sound approach whose time has come for randomized trialy. Neurorehabilitation and Neuronal Repair 1999; 13(3): 157–164).

For individuals with more severe bilateral paralysis involving the two legs, forced use of the impaired limbs and treadmill-based locomotion therapies are impractical and potentially unsafe. The patient is too impaired to move the legs independently while either freely standing or suspended over a moving treadmill belt. In these cases, stimulation therapy can be provided only by externally imposing movements of the legs in repetitive patterns resembling daily life activities such as walking.

The effectiveness of providing stimulation to individuals with bilateral paralysis by externally imposed movements of the impaired limbs has been dramatized in popular press descriptions of Christopher Reeves' medical situation. Reeves, an actor famous for his film portrayal of Superman, suffered a complete section of his spinal cord resulting in total paralysis and loss of sensation below the neck. Despite the conventional belief that his paralysis was permanent and complete, Reeves has undergone imposed movement stimulation therapy as administered by a team of clinicians for several hours per day, resulting in measurable recovery of sensory and motor function in the legs.

There are practical and technical barriers to widespread treatment of severe stroke, spinal cord injury, and traumatic brain injury patients using externally imposed movement therapy similar to that used with Reeves. When the movement therapy is provided manually, the therapy requires multiple clinicians for multiple hours per day to manipulate the limbs, making the cost of such therapy prohibitive. Even with the patient suspended on a moving treadmill belt, the assistance of multiple clinicians to manually move the legs is required, since movement of the treadmill belt alone does not result in stepping-like leg motions.

In response to increased interest in the use of imposed movement therapy, two manufacturers have developed partial weight bearing treadmill systems that include mechanically powered appendages that can automatically move the legs through pre-programmed patterns of movement. One of these devices, the "AutoAmbulator"manufactured by HealthSouth Corporation of Birmingham, AL, is described at www.healthsouth.com/medinfo/home/app.

The HealthSouth website describes the AutoAmbultor as including an overhead harness system able to fully or partially support a subject's weight, two mechanically motorized braces to move each of the subject's legs, computerized sensors to track the subject's vital signs, leg motions and speed of leg movements, devices that permit automatic belt speed adjustments based on leg movement speed, and emergency controls that permit the subject or therapist to stop the machine. The site further describes the ability of the machine to mimic the proper human gait as well as to provide the clinician with the above described data to monitor patient progress.

The HealthSouth website also provides two studies. The first study describes a normal subject walking on the AutoAmbulator system with partial weight support while wearing a tight nylon suit fitted with reflectors. The positions of the reflectors over time are recorded by a computer-video based motion analysis system. The purpose of the first study is to measure the subject's leg motions during robotic patterning and to compare the patterned motions to those produced by the same subjects during normal unassisted walking on the treadmill. The second study uses x-ray imaging techniques to analyze the position of the lower back while normal subjects are suspended in the harness six inches above the treadmill and while wearing the harness with the feet on the treadmill. The purpose of the second study is to assure that the harness system does not cause potential harm to the lower back.

A second partial weight bearing treadmill device incorporating a robotic appendage to provide patterns for movement of the legs is the LOKO System® manufactured jointly by Woodway GmbH of Weil am Rhein, Germany, and Hocoma AG of Zurich, Switzerland. The LOKO System, as described at the website www.woodway.com/LOKO_new.htm, is an open treadmill and partial weight bearing harness in which the patient can be led through locomotion therapy either with the clinician manipulating the patients leg movements or with the leg movements imposed automatically by an motorized appendage.

A number of devices and methods for measuring the forces and motions of the legs during free walking and walking on a treadmill have been described in the prior art. Examples of devices for recording the motions of the legs and body using computer-video techniques include systems manufactured by MotionAnalysis Corporation of Santa Rosa, Calif. and Vicon Ltd. of Oxford, United Kingdom, Lake Forest, Calif. and Hong Kong. Advanced Mechanical Technology, Inc. of Watertown, Mass. markets forceplates that can be mounted in the surface over which a subject walks to document the forces of the feet during human balancing and walking. The Balance Master system manufactured by NeuroCom International, Inc. of Clackamas, Oreg. uses a five-foot long forceplate to record the timing and positions of successive foot placements during locomotion. U.S. Pat. No. 5,474,087, U.S. Pat. No. 5,623,944, and U.S. Pat. No. 6,010,465 (each of which are hereby incorporated herein by reference) describe a treadmill device incorporating at least two forceplates under the moving belt to record the forces of the two legs independently during treadmill walking. GaitRite, a pressure sensitive mat manufactured by CIR Systems Inc. of Clifton, N.J. can measure the locations and timing of the successive steps of a walking subject.

SUMMARY OF THE INVENTION

In a first embodiment of the invention there is provided a method for characterizing contributions of forces associated with a body part of a subject when the body part is involved in movement. The method includes causing movement of the body part in a prescribed manner and monitoring quantities related to at least one of displacement of the body part and external force on the body part. At least one quantity related to a force contribution associated with the body part is determined from the quantities measured.

In accordance with related embodiments, the method may also include monitoring activity of a muscle associated with the body part in relation to displacement of the body part. Additionally, causing movement of the body part may include causing a large slow displacement of the body part. Similarly, causing movement of the body part may include causing a small rapid displacement of the body part. In accordance with other related embodiments, activity of a muscle associated with the body part may be monitored when the muscle is relaxed and/or activity of a muscle associated with the body part may be monitored when the muscle is active. The body part may include a limb or a set of limbs.

In accordance with further related embodiments, monitoring quantities related to displacement of the body part may include monitoring the displacement of a joint associated with the body part and the joint may be a knee. Monitoring quantities related to the displacement of the knee may include monitoring displacement along a knee-flexion-extension axis and/or monitoring displacement along a knee pronation-supination axis. Similarly, monitoring quantities related to the displacement of knee may include monitoring displacement along an eversion-inversion axis. In accordance with another related embodiment, the joint may be a hip. In addition, causing movement of the body part by the application of external force may include causing cyclic movement typical of walking.

In accordance with another embodiment of the invention, an apparatus for characterizing contributions of forces associated with a body part of a subject when the body part is involved in movement includes means for causing movement of the body part in a prescribed manner, means for monitoring quantities related to at least one of displacement of the body part and external force on the body part and means for determining at least one quantity related to a force contribution associated with the body part from the quantities measured. In accordance with related embodiments, the apparatus may include means for monitoring activity of a muscle associated with the body part in relation to displacement of the body part. Additionally, the means for causing movement of the body part may include a mechanical arm. Similarly, the means for causing movement of the body part may include an actuator. In accordance with other related embodiments, the means for monitoring displacement of the body part may include means for accepting signals for controlling the position of the body part. Further, the means for monitoring displacement of the body part may include means for generating signals for related to the position of the body part and forces generated by the body part.

In accordance with a further embodiment of the invention, an apparatus for characterizing contributions of forces associated with a body part of a subject when the body part is involved in movement includes an appendage coupled to the body part for causing movement of the body part in a prescribed manner, a measurement device that measures quantities related to at least one of displacement of the body part, external forces on the body part and forces generated by the appendage. A computational device is in communication with the measurement device for determining at least one quantity related to a force contribution associated with the body part. In accordance with a related embodiment, the apparatus may also include surface electromygraphic recorder for monitoring the activity of a muscle associated with the body part. In accordance with additional related embodiments, the computational device may calculate forces necessary to move the body part when no muscle activity is detected. Further, the body part may be a leg and the appendage attaches to the leg and causes knee and hip joints of the leg to move in patterns similar to those generated when walking. The measurement device may measure angular displacement of the knee and hip joints and/or the measurement device may measure forces generated by the appendage in rotating the knee and hip joints.

In accordance with further related embodiments, the appendage may include an actuator. Additionally, the measurement device may include an input for receiving and an output for transmitting signals related to displacement of the appendage and of the body part and forces generated by the appendage and the body part. Further, the appendage may include the measurement device. Similarly, the measurement device may be integrated with an actuator. In accordance with another related embodiment, the apparatus may include a display for displaying the at least one quantity related to a force contribution associated with the body part to a clinician. Similarly, the apparatus may include a display for displaying the at least one quantity related to a force contribution associated with the body part to the subject.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

When a portion of a subject's body, for example a limb, is moved by an externally attached mechanical device or appendage, the force required to impose a movement on the limb is related to the combined effects of the physical mass of the limb, the passive visco-elastic properties of the limb, and any active muscular forces generated by the limb either in support of or opposition to the imposed motion. Given knowledge of the physical dimensions and mass of the limb, the external force required to move a passive limb (i.e., a limb displaying no active muscular forces) may be calculated using classical Newtonian mechanics. Thus, with knowledge of the masses of the limb segments, the positions and degrees-of-freedom of the joints linking the limb segments, Newtonian mechanics, and the forces generated by a motorized mechanical device driving the limb motion, it is possible to determine the passive inertial, elastic, viscous components of the driving force. Any additional component of force not attributable to the above three components may be attributed to the active muscular force component.

It is further possible to differentiate between the contributions of the passive elastic, viscous, and non-visco-elastic active muscular components of the musculoskeletal force using principles of classical Newtonian mechanics. Specifically, it is known that the forces related to the elastic properties of a moving mass are in opposition and proportional to the displacement of the mass from a neutral rest position, whereas force contributed by the viscous property is also in opposition and proportional to rate of displacement.

The force generating properties of individual human muscles and pairs of muscles acting in opposition to one another about a body joint, termed antagonist pairs, are well described in the prior art (Principles of Neural Science. Kandel & Schwaretz, editors. Elsevier/North Holland, N.Y., 1981). When one of an antagonistic pair of muscles is neurally activated, a muscular driving force is generated tending to move the joint in the direction of the active muscle, with the driving force proportional to the level of the neural activation. When both muscles of an antagonistic pair are simultaneously and equally activated, termed co-activation, no driving force tending to move the joint is generated. During the co-activation state, however, the elastic resistance of the joint to an externally imposed displacement increases, with the active component of the elastic resistance proportional to the level of co-activation. Finally, when an antagonistic pair of muscles undergoes unequal co-activation, the result is combination of a muscular driving force tending to move the joint in the direction of the more active muscle and an increased active elastic component. In this case, the muscular driving force is related to the difference in levels of activation of the two antagonist muscles, while the active elastic component is related to the activation level of the muscle undergoing the lesser activation.

By imposing movements about the joint of a limb using an attached mechanical device or attached appendage and measuring the forces required to generate such imposed movement, it is possible to isolate the effects of the passive elastic, passive viscous, active elastic, and muscular driving force components. For example, by moving the limb through large displacement amplitudes at very slow displacement rates it is possible to maximize the effect of the passive elastic component of force while minimizing the inertial and passive viscous components. Under this condition of imposed motion, the elastic component is the force directly related to limb position, while the muscular driving force component is unrelated to position. Then, small, rapid displacements of the limb are used to maximize the viscous component and minimize the elastic. Now, the viscous component is the force directly related to limb displacement rate while the muscular driving force component is the force unrelated to displacement.

By combining the above methods with additional methods for measuring the level of activation of individual muscles, it is further possible to isolate the effects of the passive elastic forces from the active elastic forces generated by to the co-activation of antagonist muscles. One quantitative method for measuring the level of neural activation of a muscle uses surface electromyographic ("EMG") recording techniques well-known in the prior art. A second method for measuring the activation level of a muscle is for a trained clinician to manually press on the belly of the muscle and then observe the degree of muscle hardness. One method of recording the passive elastic and viscous forces is to move the limb according to the above described methods, monitor the EMG activity level of the muscle, or the degree of muscle belly hardness, to assure that the antagonistic muscles are not active, and record the passive elastic and viscous components. During subsequent movements of the limb, differences in recorded elastic forces are related to the active elastic force, while the force component unrelated to the limb displacement is related to the muscular driving force component.

Using the above described methods, it is possible to cause a multi-segmented limb to move about several joints at the same time and to determine the passive, elastic, viscous, and active muscle components of force acting about each of the moving joints separately. For example, an appendage such as that described for the AutoAmbulator may be used to move the knee and hip joints in a cyclic pattern resembling normal walking. The above described measurements may be performed with the limb moving while suspended or while moving in contact with the moving belt of a treadmill.

Since the typical human limb joint can move about more that one axis at a time, the above described methods can be further used to determine the passive, elastic, passive viscous, active elastic, and active force components acting about different axes of limb joint motion. Using the example of cyclic knee and hip joint motions typical of walking, the inertial, elastic, viscous, and active muscular force components acting at the knee joint may be determined for not only the normal axis of bending (the knee flexion-extension axis) but also for the axis of lateral twisting motion (knee pronation-supination) and the axis of longitudinal twisting motion (eversion-inversion).

The ability to quantify during imposed movement therapy the extent to which a patient contributes effort to generation of the imposed movement compared to the extent generated by the forces and motions of the motorized appendage would provide several forms of clinically useful information. First, the information would be useful to assure the safety of imposed movement therapy using a powered appendage. One example would be a subject whose knee joint motion is severely restricted about a specific axis of motion. In the absence of any information related to the elastic and viscous components, the powered appendage might continue to force the knee into positions causing further damaging the joint. With the information provided by the proposed devices, maximum levels of elastic, viscous, and active muscular forces may be established and motions of the appendage halted or otherwise modified whenever one more of these force levels are exceeded.

Further, the information may be used as a measure of treatment progress. Specifically, as a patient's improves over time, the percentage of the movement generated by the efforts of the patient will increase, while that imposed by the motorized appendage will decrease.

In addition, the information may be used as a measure of the effectiveness of the pattered movement therapy. Imposed movement therapy may be problematic in patients with excess spasticity or excessive co-activation of antagonistic muscles, for examples. Spasticity is a condition that causes a paralyzed limb to react reflexively so as to actively resist externally imposed movements such as those provided by the motorized appendage. In the case of imposed movement therapy, the spastic reflex reactions may contribute inappropriately in that they would generate forces actively resisting rather than supporting the motions imposed by the appendage. In patients with excessive co-activation of antagonistic pairs of muscles, the joints of the limb become excessively stiff and thereby also tend to actively resist rather than support the motions imposed by the motorized appendage. Thus, information related to the quality of the patient's contribution to the imposed movement may allow the clinician to modify the pattern of the movement to reduce the confounding effects of spactisity and co-activation or otherwise to take other medical actions to reduce these adverse effects.

Finally, the information may be used as a biofeedback signal provided to the patient and the supervising clinician during the patterned movement therapy. As the patient struggles to regain active control over the paralyzed limbs during the imposed movement therapy and as the treating clinician works to assist in this effort, the biofeedback signal can provide immediate information related to the effectiveness of the subject's efforts as well as help focus effort on those actions having the greatest positive impact on performance. Such biofeedback information is particularly valuable, because a paralyzed patient may be unable to accurately sense how his or her actions contribute to the imposed movement, which in the absence of biofeedback may lead to discouragement and loss of motivation. Embodiments of this invention therefore address such problems.

Figure 1:
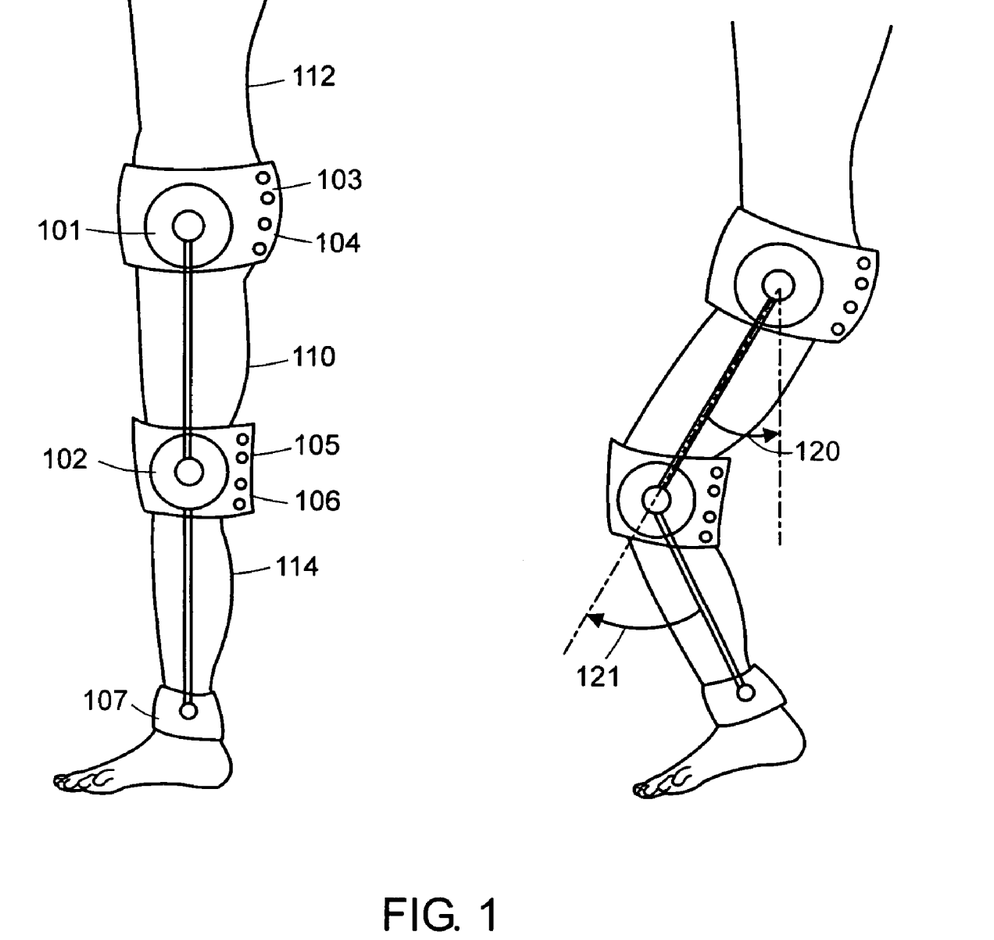
FIG. 1 is graphical illustration of a mechanical device for moving knee and hip joints in a prescribed pattern in accordance with an embodiment of the invention.

FIG. 1 is graphical illustration of a mechanical device for moving knee and hip joints in a prescribed pattern in accordance with an embodiment of the invention. A combination trunk brace and hip actuator 101 is coupled to the subject's body at the hip. The trunk brace and hip actuator 101 is used to move the upper leg segment 110 relative to the trunk 112 about the hip joint. In accordance with this embodiment, the trunk brace and hip actuator includes at least one input or signal receiver 103 for accepting signals used to control the position of the hip actuator 101 and thus cause motion of the hip in a prescribed manner. At least one output or signal transmitter 104 provides signals related to the position of the hip joint and the forces generated by the hip actuator 101.

The device also includes a combination upper leg brace and knee actuator 102 which is coupled to the subject's knee. The upper leg brace and knee actuator 102 is used to move the lower leg segment 114 relative to the upper leg segment 110 about the knee joint. Again, the upper leg brace and knee actuator includes at least one input or signal receiver 105 for accepting signals used to control the position of the knee actuator and consequently cause motion of the knee in a prescribed manner. At least one output or signal transmitter provides signals related to the position of the knee joint and the forces generated by the knee actuator. The device further includes a lower leg segment brace 107 which is coupled to the knee joint actuator 102. By employing this embodiment, the upper leg brace and knee actuator is continually coupled to the knee joint even when the knee joint is in a flexed position relative to the upper leg, as shown at 121. Similarly, the trunk brace and hip actuator stays coupled to the hip joint even with the hip joint in a flexed position relative to the trunk as shown at 120.

Figure 2:
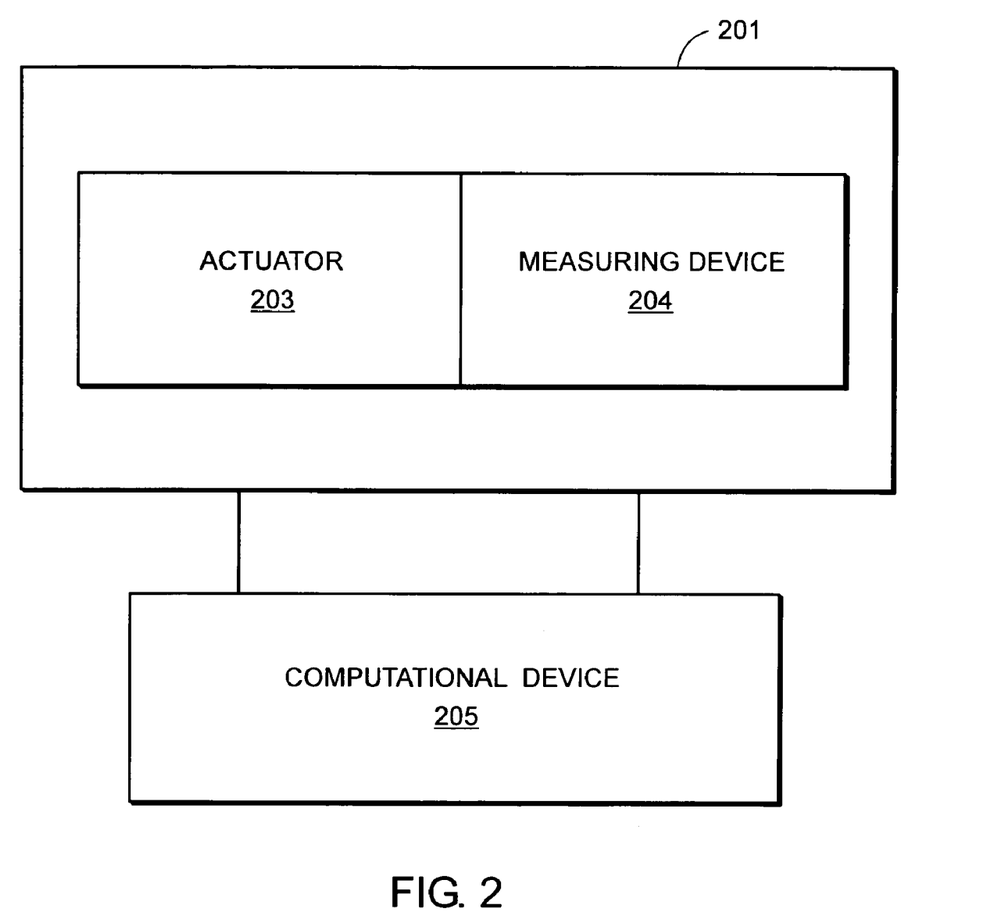
FIG. 2 is a block diagram illustrating an apparatus for characterizing contributions of forces associated with a body part of a subject in accordance with an embodiment of the invention.

FIG. 2 is a block diagram illustrating an apparatus for characterizing contributions of forces associated with a body part of a subject in accordance with an embodiment of the invention. The apparatus includes an appendage 201 which is coupled to the body part of the subject. The appendage 201, which may be designed as brace as shown with respect to FIG. 1, or a mechanical device, such as a robotic arm, causes movement of the body part in a prescribed manner. For example, the appendage 201 may cause the body part to move (i) through large displacement amplitudes at very slow displacement rates in order to maximize the effect of the elastic component of force while minimizing the viscous component of force and (ii) through, small, rapid displacements to maximize the viscous component of force as described above. Similarly, the appendage 201 may cause the body part to move in a manner that the body part would move during normal physical activity. For example, the appendage may attach to the leg of the subject and cause knee and hip joints of the leg to move in patterns similar to those generated when walking. To this end, the appendage may include an actuator 203.

A measurement device 204 measures quantities related to at least one of displacement of the body part, external forces on the body part, or forces generated by the motorized appendage as it imposes a displacement on the body part. For example, the measurement device 203 may measure angular displacement of the knee and hip joints and/or forces generated by the appendage in rotating the knee and hip joints. The measurement device may include an input for receiving and an output for transmitting signals related to displacement of the appendage and of the body part and/or signals related to forces generated by the appendage and the body part as shown in FIG. 1. The measurement device 204 may be included in the appendage 201, as shown here, or it may simply be coupled to the appendage as shown in FIG.

Figure 3:
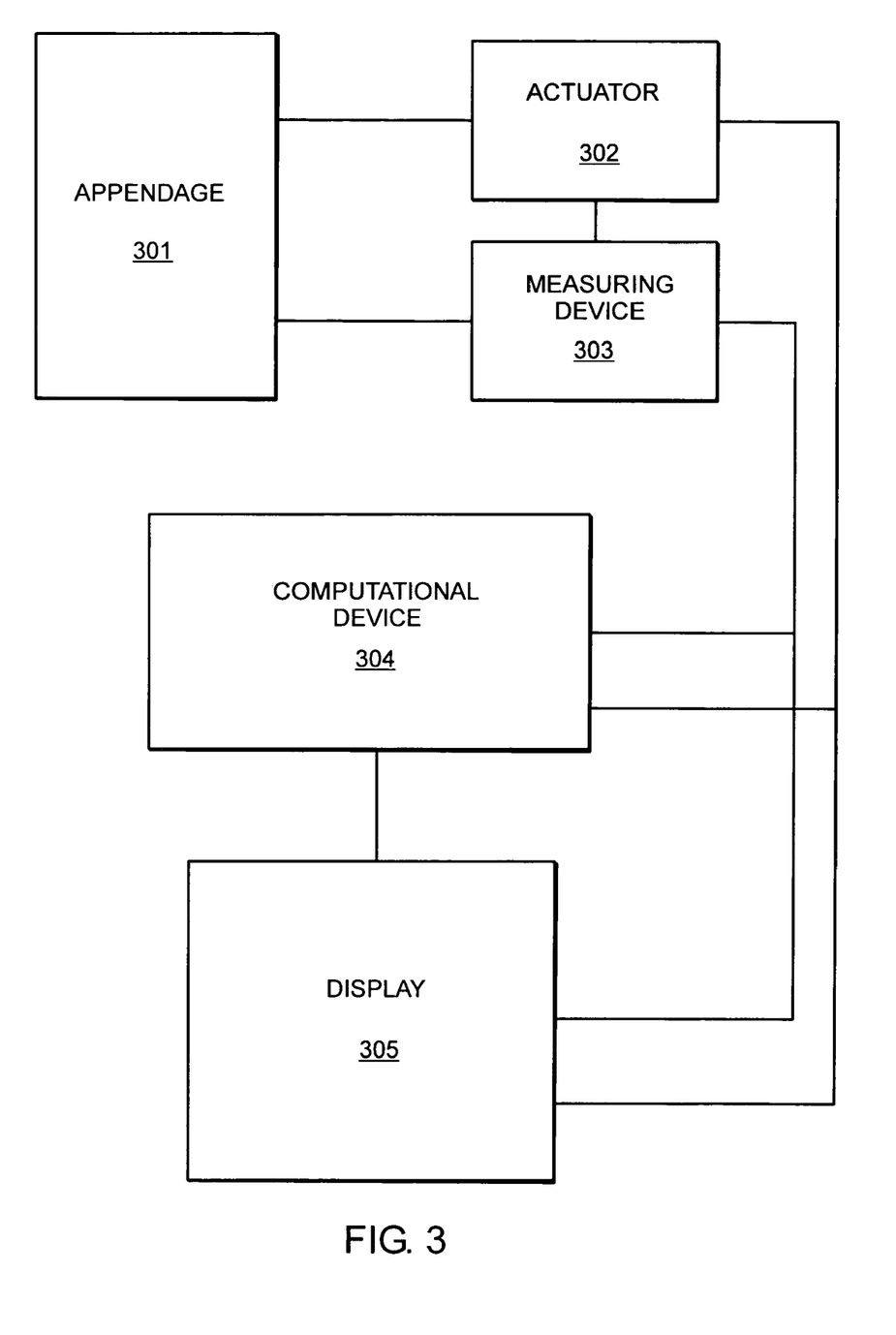
FIG. 3 is a block diagram illustrating is an apparatus for characterizing contributions of forces associated with a body part of a subject in accordance with a further embodiment of the invention.

3. Similarly, the measurement device may be integrated with the actuator 203.

A computational device 205 is in communication with the measurement device 204. The computation device 205 determines at least one quantity related to a force contribution associated with the body part. The computational device may calculate forces necessary to move the body part when no muscle activity is detected. The computational device 205 may also be in communication with the actuator 203 in order to provide control signals for controlling the actuator. The computation device 205 may also be in communication with a surface electromygraphic recorder (not shown) which monitors the activity of a muscle associated with the body part.

FIG. 3 is a block diagram illustrating is an apparatus for characterizing contributions of forces associated with a body part of a subject in accordance with a further embodiment of the invention. In accordance with this embodiment, the measuring device 302 and actuator 303 are not integrated with the appendage 301. The appendage 301 is coupled to the actuator 302 and measuring device 303 which may also be coupled to one another. A computation device 304 is coupled to the actuator 302 and the measuring device 303. A display 305 may be coupled to the computational device 304 for displaying at least one quantity related to a force contribution associated with the body part to a clinician, such as a health care provider or therapist, or to the subject. The display 305 may also display data provided to the computational device as an input.

Figure 4:
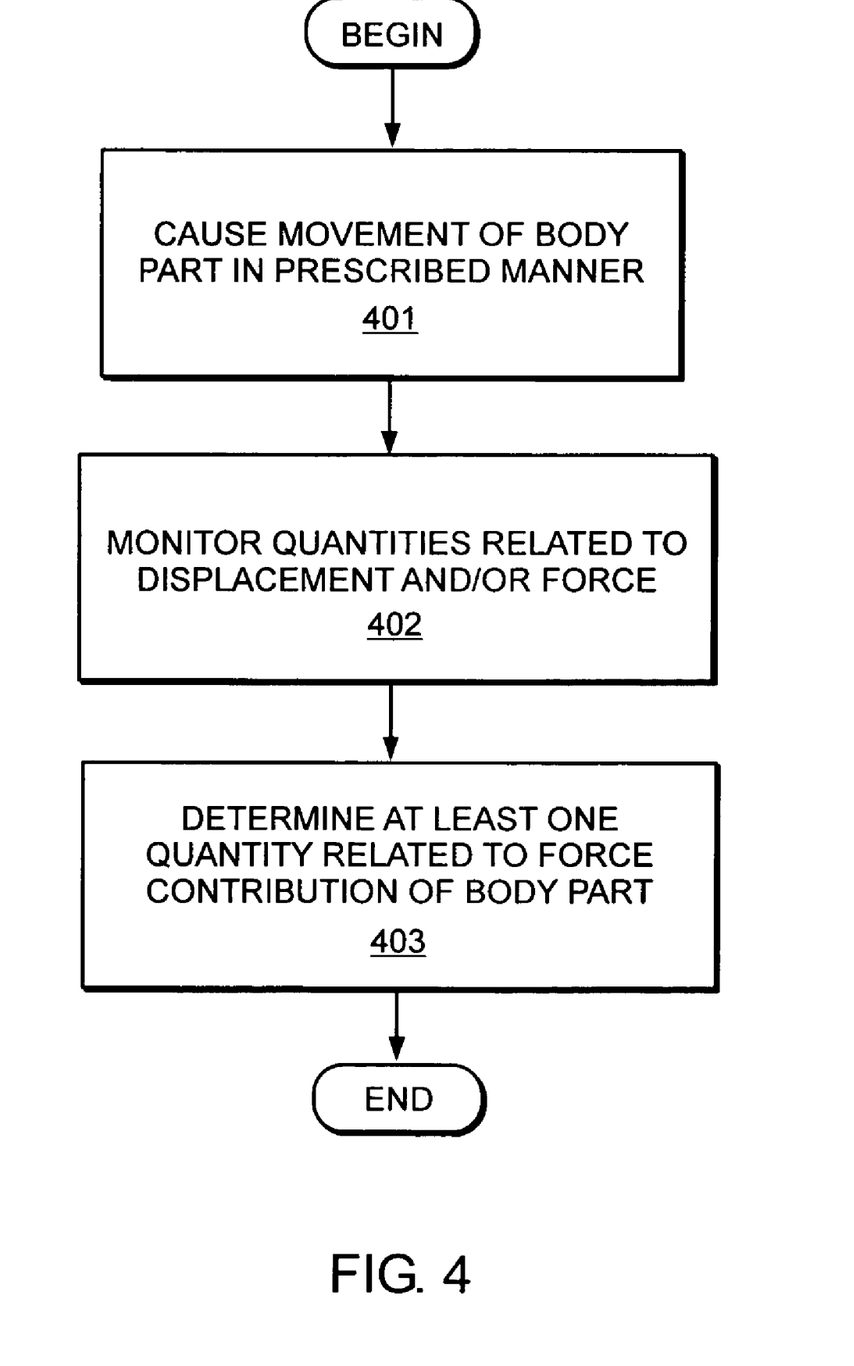
FIG. 4 is a flow chart illustrating a method for characterizing contributions of forces associated with a body part of a subject in accordance with a further embodiment of the invention.

FIG. 4 is a flow chart illustrating a method for characterizing contributions of forces associated with a body part of a subject in accordance with a further embodiment of the invention. In process 401, an appendage or mechanical device or a clinician, therapist or other health care provider causes the body part to be moved in a prescribed manner. For example, causing movement of the body part may include causing cyclic movement of a leg typical of walking. Quantities related to at least one of displacement of the body part and external force on the body part are monitored in process 402. Monitoring quantities related to displacement may include monitoring quantities related to the displacement of a joint associated with the body such as monitoring quantities related to the displacement along a knee-flexion-extension axis, a knee pronation-supination axis and/or an eversion-inversion axis. Activity of a muscle associated with the body part may also be monitored when the body part is active and/or when the body part is relaxed. At least one quantity related to a force contribution associated with the body part is then determined 403 from the quantities measured.

While the invention has been described in connection with specific embodiments thereof, it will be understood that it is capable of further modification. This application is intended to cover any variation, uses, or adaptations of the invention and including such departures from the present disclosure as come within known or customary practice in the art to which invention pertains.

What is claimed is:

1. A method for characterizing contributions of forces associated with a body part of a subject when the body part is involved in movement, the method comprising:

applying external forces to the body so as to cause movement of the body part in a first manner and a second manner, wherein the first manner includes causing a large displacement of the body part at a slow displacement rate and the second manner includes causing a small displacement of the body part at a rapid displacement rate, wherein the body part exerts an internal force to contribute to the movement of the body part;

monitoring quantities related to the displacements of the body part and the external forces applied to the body part; and determining at least one quantity related to the contribution of the internal force generated by the body part from the quantities measured.

2. A method according to claim 1, further comprising:
monitoring activity of a muscle associated with the body part in relation to the displacements of the body part.

3. A method according to claim 1, further comprising;
monitoring activity of a muscle associated with the body part when the muscle is relaxed.

4. A method according to claim 1, further comprising:
monitoring activity of a muscle associated with the body part when the muscle is active.

5. A method according to claim 1, wherein the body part includes a limb.

6. A method according to claim 1, wherein the body part includes a set of limbs.

7. A method according to claim 1, wherein monitoring quantities related to the displacements of the body part includes monitoring a displacement of a joint associated with the body part.

8. A method according to claim 7, wherein the joint is a knee.

9. A method according to claim 8, wherein monitoring quantities related to the displacement of the knee includes monitoring displacement along a knee-flexion-extension axis.

10. A method according to claim 8, wherein monitoring quantities related to the displacement of the knee includes monitoring displacement along a knee pronation-supination axis.

11. A method according to claim 8, wherein monitoring quantities related to the displacement of the knee includes monitoring displacement along an eversion-inversion axis.

12. A method according to claim 7, wherein the joint is a hip.

13. A method according to claim 1, wherein causing movement of the body part further includes causing cyclic movement typical of walking.

* * * * *